US010894089B2

(12) United States Patent
Heo et al.

(10) Patent No.: US 10,894,089 B2
(45) Date of Patent: Jan. 19, 2021

(54) LONG-ACTING INSULIN OR INSULIN ANALOGUE CONJUGATE

(71) Applicant: HANMI PHARM. CO., LTD., Hwaseong-si (KR)

(72) Inventors: Yong Ho Heo, Hwaseong-si (KR); Jong Soo Lee, Hwaseong-si (KR); Sung Hee Park, Hwaseong-si (KR); Dae Jin Kim, Hwaseong-si (KR); Sung Youb Jung, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 55 days.

(21) Appl. No.: 15/551,489

(22) PCT Filed: Feb. 17, 2016

(86) PCT No.: PCT/KR2016/001628
§ 371 (c)(1),
(2) Date: Aug. 16, 2017

(87) PCT Pub. No.: WO2016/133372
PCT Pub. Date: Aug. 25, 2016

(65) Prior Publication Data
US 2018/0161448 A1    Jun. 14, 2018

(30) Foreign Application Priority Data
Feb. 17, 2015  (KR) .................. 10-2015-0024091

(51) Int. Cl.
A61K 38/28      (2006.01)
A61K 47/68      (2017.01)
C07K 14/62      (2006.01)
A61K 47/50      (2017.01)
A61K 47/60      (2017.01)
A61P 3/10       (2006.01)
C12N 15/67      (2006.01)
A61K 38/00      (2006.01)

(52) U.S. Cl.
CPC .......... A61K 47/6811 (2017.08); A61K 38/28 (2013.01); A61K 47/50 (2017.08); A61K 47/60 (2017.08); A61P 3/10 (2018.01); C07K 14/62 (2013.01); C12N 15/67 (2013.01); A61K 38/00 (2013.01); C07K 2317/52 (2013.01); C07K 2317/522 (2013.01); C07K 2317/524 (2013.01); C07K 2317/526 (2013.01); C07K 2317/528 (2013.01); C07K 2317/53 (2013.01); C07K 2319/30 (2013.01); C12N 2840/203 (2013.01)

(58) Field of Classification Search
CPC ............................ A61K 47/4811; C07K 14/62
See application file for complete search history.

(56) References Cited

U.S. PATENT DOCUMENTS

| | | | | |
|---|---|---|---|---|
| 9,492,507 | B2* | 11/2016 | Song | A61K 38/28 |
| 10,046,061 | B2* | 8/2018 | Jang | A61K 38/28 |
| 2013/0028918 | A1* | 1/2013 | Song | A61K 38/28 |
| | | | | 424/179.1 |
| 2016/0000931 | A1* | 1/2016 | Jang | A61K 38/28 |
| | | | | 530/391.9 |

FOREIGN PATENT DOCUMENTS

| | | |
|---|---|---|
| CN | 103509118 A | 1/2014 |
| EP | 1366067 B1 | 9/2012 |
| KR | 10-2011-0111267 A | 10/2011 |
| KR | 10-2015-0008012 A | 1/2015 |
| WO | 96/032478 A1 | 10/1996 |
| WO | 97/034631 A1 | 9/1997 |
| WO | 2009/015345 A1 | 1/2009 |
| WO | 2010/107520 A1 | 9/2010 |
| WO | 2011/122921 A2 | 10/2011 |
| WO | 2013/096386 A1 | 6/2013 |
| WO | 2014/017847 A1 | 1/2014 |

OTHER PUBLICATIONS

Liu et al., JBC 278: 14798-14805, ( 2003).*
Mcauley et al. Protein Sci. 17: 95-106, (2008).*
Wozniak-Knopp, Plos One 7: e30083, (2012).*
Allison J. Hahr, et al., "Optimizing Insulin Therapy in Patients with Type 1 and Type 2 Diabetes Mellitus: Optimal Dosing and Timing in the Outpatient Setting", DM, Mar. 2010, pp. 148-162.
International Search Report for PCT/KR2016/001628 dated Aug. 19, 2016 [PCT/ISA/210].
Written Opinion for PCT/KR2016/001628 dated Aug. 19, 2016 [PCT/ISA/237].
European Patent Office; Communication dated Aug. 3, 2018 in counterpart EP application No. 16752702.7.

* cited by examiner

Primary Examiner — Gyan Chandra
(74) Attorney, Agent, or Firm — Sughrue Mion, PLLC

(57) ABSTRACT

The present invention relates to insulin and/or an insulin analogue conjugate, and a use thereof, wherein the insulin and/or insulin analogue have improved in vivo durability and stability by linking the same with an Fc region of immunoglobulin. The insulin and/or an insulin analogue conjugate of the present invention show an in vivo activity similar to that of insulin. In addition, the insulin and/or insulin analogue conjugate of the present invention are long-acting formulations of insulin and/or the analogue thereof, in which serum half-life is remarkably increased, and therefore, the present invention provides remarkable insulin and/or an insulin analogue conjugate, which do not induce hypoglycemia, a drawback of insulin treatment.

15 Claims, No Drawings
Specification includes a Sequence Listing.

SEQUENCE LISTING

<160> NUMBER OF SEQ ID NOS: 24

<210> SEQ ID NO 1
<211> LENGTH: 21
<212> TYPE: PRT
<213> ORGANISM: Artificial Sequence
<220> FEATURE:
<223> OTHER INFORMATION: Synthetic construct of A chain of insulin

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
        20

<210> SEQ ID NO 2
<211> LENGTH: 30
<212> TYPE: PRT
<213> ORGANISM: Artificial Sequence
<220> FEATURE:
<223> OTHER INFORMATION: Synthetic construct of B chain of insulin

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 765
<212> TYPE: DNA
<213> ORGANISM: Artificial Sequence
<220> FEATURE:
<223> OTHER INFORMATION: Synthetic construct of A chain-IgG1 Fc(S171H/
      F212A)

<400> SEQUENCE: 3
atgggcattg tggaacagtg ctgtaccagc atttgtagtc tatatcaact tgaaaattat    60
tgtaatgagc ccaaatcatg cgataaaacc cacacctgtc ccccatgccc ggctccggaa   120
ctcttaggtg gccctagcgt atttctgttc ccgccgaagc cgaaggatac gctgatgatc   180
tcacggaccc cagaagttac ttgcgtggtg gtggacgtat cacatgaaga tcccgaggtc   240
aaatttaatt ggtacgttga tggggttgaa gtacataatg caaaaacaaa gccgcgtgag   300
gagcagtata attcaactta tcgtgtggtc agcgtgctga cagttctgca ccaggattgg   360
ctcaacggga agaatataaa gtgtaaagtt tccaacaaag ccctgccagc tcctatagag   420
aaaactatct cgaaagccaa aggacagcca cgtgaacctc aggtttacac gctgccaccg   480
tcccgcgatg aattaacaaa aaatcaggtg catttgacgt gtctggttaa gggtttctat   540
ccgagcgaca ttgcggtaga atgggaatct aatggacaac tgagaataa ctacaaaact   600 acaccgccgg ttttagatag cgatggttcc tttgcgcttt atagcaaact gacggtggac   660
aaaagtcgtt ggcagcaagg caacgtcttt agttgcagcg tcatgcatga agcacttcac   720
aaccattaca cccagaaatc tctgagcctg tcgcctggta agtag             765

<210> SEQ ID NO 4
<211> LENGTH: 254
<212> TYPE: PRT
<213> ORGANISM: Artificial Sequence
<220> FEATURE:
<223> OTHER INFORMATION: Synthetic construct of A chain-IgG1 Fc(S171H/
      F212A)

<400> SEQUENCE: 4

Met Gly Ile Val Glu Gln Cys Cys Thr Ser Ile Cys Ser Leu Tyr Gln
1               5                   10                  15

Leu Glu Asn Tyr Cys Asn Glu Pro Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
    50                  55                  60

```
Glu Val Thr Cys Val Val Val Asp Val Ser His Glu Asp Pro Glu Val
 65                  70                  75                  80

Lys Phe Asn Trp Tyr Val Asp Gly Val Glu Val His Asn Ala Lys Thr
                 85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val His Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Ala Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 5
<211> LENGTH: 792
<212> TYPE: DNA
<213> ORGANISM: Artificial Sequence
<220> FEATURE:
<223> OTHER INFORMATION: Synthetic construct of B chain-IgG1 Fc(Y165T/
      T209F)

<400> SEQUENCE: 5
atgtttgtaa atcaacatct gtgtgggagt caccttgtgg aagcattata tttagtctgc      60
ggtgaacgtg gattcttcta cactcctaaa actgaaccga agtcatgcga taagacccat     120
acgtgtccgc cctgtcccgc cccggaactg cttggcggcc ctagtgtttt tctgtttcct     180
ccgaaaccaa aagatacgtt gatgattagc agaacgccgg aagttacctg tgtagtcgtt     240
gacgtatccc acgaagatcc ggaggtgaaa ttcaattggt atgttgatgg tgtggaggtg     300
cataatgcca aaacgaaacc tcgtgaagag cagtataact ctacctaccg cgtcgtaagc     360
gtgctgacag ttctccatca ggactggctg aatggtaaag agtataaatg caaagttagt     420
aacaaggctc tgcctgctcc catagaaaaa accatctcta aagcgaaggg tcagccgcgg     480
gagccacaag ttacaaccct gccaccgtct cgcgacgaat taaccaagaa tcaggtgtcc     540
ctgacatgcc tagtcaaggg cttttatccc agtgatattg cggtggaatg ggaatcgaat     600
ggacaaccag aaaacaacta caaaactttc ccgccagtcc tggactcaga tggcagcttt     660
tttctgtatt ctaaactcac agtggataaa tcgcgttggc agcaggggaa cgtgtttagc     720
tgtagcgtga tgcatgaggc actgcacaat cattatactc agaaatccct ttcattaagc     780
cctggaaaat ag                                                         792

<210> SEQ ID NO 6
<211> LENGTH: 263
```

<212> TYPE: PRT
<213> ORGANISM: Artificial Sequence
<220> FEATURE:
<223> OTHER INFORMATION: Synthetic construct of B chain-IgG1 Fc(Y165T/
      T209F)

<400> SEQUENCE: 6

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr Glu
            20                  25                  30

Pro Lys Ser Cys Asp Lys Thr His Thr Cys Pro Pro Cys Pro Ala Pro
        35                  40                  45

Glu Leu Leu Gly Gly Pro Ser Val Phe Leu Phe Pro Pro Lys Pro Lys
    50                  55                  60

Asp Thr Leu Met Ile Ser Arg Thr Pro Glu Val Thr Cys Val Val Val
65                  70                  75                  80

Asp Val Ser His Glu Asp Pro Glu Val Lys Phe Asn Trp Tyr Val Asp
                85                  90                  95

Gly Val Glu Val His Asn Ala Lys Thr Lys Pro Arg Glu Glu Gln Tyr
            100                 105                 110

Asn Ser Thr Tyr Arg Val Val Ser Val Leu Thr Val Leu His Gln Asp
        115                 120                 125

Trp Leu Asn Gly Lys Glu Tyr Lys Cys Lys Val Ser Asn Lys Ala Leu
    130                 135                 140

Pro Ala Pro Ile Glu Lys Thr Ile Ser Lys Ala Lys Gly Gln Pro Arg
145                 150                 155                 160

Glu Pro Gln Val Thr Thr Leu Pro Pro Ser Arg Asp Glu Leu Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Phe Pro Pro Val Leu Asp Ser Asp Gly Ser Phe Phe Leu Tyr Ser
    210                 215                 220

Lys Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Pro Gly Lys
            260

<210> SEQ ID NO 7
<211> LENGTH: 36
<212> TYPE: DNA
<213> ORGANISM: Artificial Sequence
<220> FEATURE:
<223> OTHER INFORMATION: Synthetic construct of Sequence containg
      ribosome binding site

<400> SEQUENCE: 7
aataattttg tttaacttta agaaggagat atacaa                            36

<210> SEQ ID NO 8
<211> LENGTH: 66
<212> TYPE: DNA
<213> ORGANISM: Artificial Sequence
<220> FEATURE:
<223> OTHER INFORMATION: Synthetic construct of A chain of A chain-IgG1

Fc(S171H/F212A)

<400> SEQUENCE: 8
atgggcattg tggaacagtg ctgtaccagc atttgtagtc tatatcaact tgaaaattat    60
tgtaat                                                               66

<210> SEQ ID NO 9
<211> LENGTH: 45
<212> TYPE: DNA
<213> ORGANISM: Artificial Sequence
<220> FEATURE:
<223> OTHER INFORMATION: Synthetic construct of IgG1 hinge of A chain-
      IgG1 Fc(S171H/F212A)

<400> SEQUENCE: 9
gagcccaaat catgcgataa aacccacacc tgtccccat gcccg                     45

<210> SEQ ID NO 10
<211> LENGTH: 330
<212> TYPE: DNA
<213> ORGANISM: Artificial Sequence
<220> FEATURE:
<223> OTHER INFORMATION: Synthetic construct of IgG1 CH2 of A chain-IgG1
      Fc(S171H/F212A)

<400> SEQUENCE: 10
gctccggaac tcttaggtgg ccctagcgta tttctgttcc cgccgaagcc gaaggatacg    60
ctgatgatct cacggacccc agaagttact tgcgtggtgg tggacgtatc acatgaagat   120
cccgaggtca aatttaattg gtacgttgat ggggttgaag tacataatgc aaaaacaaag   180
ccgcgtgagg agcagtataa ttcaacttat cgtgtggtca gcgtgctgac agttctgcac   240
caggattggc tcaacgggaa agaatataag tgtaaagttt ccaacaaagc cctgccagct   300
cctatagaga aactatctc gaaagccaaa                                    330

<210> SEQ ID NO 11
<211> LENGTH: 324
<212> TYPE: DNA
<213> ORGANISM: Artificial Sequence
<220> FEATURE:
<223> OTHER INFORMATION: Synthetic construct of IgG1 CH3 of A chain-IgG1
      Fc(S171H/F212A)

<400> SEQUENCE: 11
ggacagccac gtgaacctca ggtttacacg ctgccaccgt cccgcgatga attaacaaaa    60
aatcaggtgc atttgacgtg tctggttaag ggtttctatc cgagcgacat tgcggtagaa   120
tgggaatcta atggacaacc tgagaataac tacaaaacta caccgccggt tttagatagc   180
gatggttcct ttgcgcttta tagcaaactg acggtggaca aaagtcgttg gcagcaaggc   240 aacgtctta gttgcagcgt catgcatgaa gcacttcaca accattacac ccagaaatct   300
ctgagcctgt cgcctggtaa gtag                                         324

<210> SEQ ID NO 12
<211> LENGTH: 22
<212> TYPE: PRT
<213> ORGANISM: Artificial Sequence
<220> FEATURE:
<223> OTHER INFORMATION: Synthetic construct of A chain of A chain-IgG1
      Fc(S171H/F212A)

<400> SEQUENCE: 12

Met Gly Ile Val Glu Gln Cys Cys Thr Ser Ile Cys Ser Leu Tyr Gln

Leu Glu Asn Tyr Cys Asn
            20

<210> SEQ ID NO 13
<211> LENGTH: 15
<212> TYPE: PRT
<213> ORGANISM: Artificial Sequence
<220> FEATURE:
<223> OTHER INFORMATION: Synthetic construct of IgG1 hinge of A chain-
      IgG1 Fc(S171H/F212A)

<400> SEQUENCE: 13

Glu Pro Lys Ser Cys Asp Lys Thr His Thr Cys Pro Pro Cys Pro
1               5                   10                  15

<210> SEQ ID NO 14
<211> LENGTH: 110
<212> TYPE: PRT
<213> ORGANISM: Artificial Sequence
<220> FEATURE:
<223> OTHER INFORMATION: Synthetic construct of IgG1 CH2 of A chain-IgG1
      Fc(S171H/F212A)

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 15
<211> LENGTH: 107
<212> TYPE: PRT
<213> ORGANISM: Artificial Sequence
<220> FEATURE:
<223> OTHER INFORMATION: Synthetic construct of IgG1 CH3 of A chain-IgG1
      Fc(S171H/F212A)

<400> SEQUENCE: 15

Gly Gln Pro Arg Glu Pro Gln Val Tyr Thr Leu Pro Pro Ser Arg Asp
1               5                   10                  15

Glu Leu Thr Lys Asn Gln Val His Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Tyr Ser Lys Leu Thr Val Asp Lys Ser Arg Trp Gln Gln Gly
65              70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
        100                 105

<210> SEQ ID NO 16
<211> LENGTH: 93
<212> TYPE: DNA
<213> ORGANISM: Artificial Sequence
<220> FEATURE:
<223> OTHER INFORMATION: Synthetic construct of B chain of B chain-IgG1
      Fc(Y165T/T209F)

<400> SEQUENCE: 16
atgtttgtaa atcaacatct gtgtgggagt caccttgtgg aagcattata tttagtctgc    60
ggtgaacgtg gattcttcta cactcctaaa act                                 93

<210> SEQ ID NO 17
<211> LENGTH: 45
<212> TYPE: DNA
<213> ORGANISM: Artificial Sequence
<220> FEATURE:
<223> OTHER INFORMATION: Synthetic construct of IgG1 hinge of B chain-
      IgG1 Fc(Y165T/T209F)

<400> SEQUENCE: 17
gaaccgaagt catgcgataa gacccatacg tgtccgccct gtccc                    45

<210> SEQ ID NO 18
<211> LENGTH: 330
<212> TYPE: DNA
<213> ORGANISM: Artificial Sequence
<220> FEATURE:
<223> OTHER INFORMATION: Synthetic construct of IgG1 CH2 of B chain-
      IgG1 Fc(Y165T/T209F)

<400> SEQUENCE: 18
gccccggaac tgcttggcgg ccctagtgtt tttctgtttc ctccgaaacc aaaagatacg    60
ttgatgatta gcagaacgcc ggaagttacc tgtgtagtcg ttgacgtatc ccacgaagat   120
ccggaggtga aattcaattg gtatgttgat ggtgtggagg tgcataatgc caaaacgaaa   180
cctcgtgaag agcagtataa ctctacctac cgcgtcgtaa gcgtgctgac agttctccat   240
caggactggc tgaatggtaa agagtataaa tgcaaagtta gtaacaaggc tctgcctgct   300
cccatagaaa aaaccatctc taaagcgaag                                    330

<210> SEQ ID NO 19
<211> LENGTH: 324
<212> TYPE: DNA
<213> ORGANISM: Artificial Sequence
<220> FEATURE:
<223> OTHER INFORMATION: Synthetic construct of IgG1 CH3 of B chain-IgG1
      Fc(Y165T/T209F)

<400> SEQUENCE: 19
ggtcagccgc gggagccaca agttacaacc ctgccaccgt ctcgcgacga attaaccaag    60
aatcaggtgt ccctgacatg cctagtcaag gctttttatc ccagtgatat tgcggtggaa   120
tgggaatcga atggacaacc agaaaacaac tacaaaactt tcccgccagt cctggactca   180
gatggcagct tttttctgta ttctaaactc acagtggata atcgcgttg gcagcagggg    240 aacgtgttta gctgtagcgt gatgcatgag gcactgcaca atcattatac tcagaaatcc   300
ctttcattaa gccctggaaa atag                                          324

<210> SEQ ID NO 20
<211> LENGTH: 31
<212> TYPE: PRT
<213> ORGANISM: Artificial Sequence
<220> FEATURE:
<223> OTHER INFORMATION: Synthetic construct of B chain of B chain-IgG1
      Fc(Y165T/T209F)

<400> SEQUENCE: 20

Met Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr
            20                  25                  30

<210> SEQ ID NO 21
<211> LENGTH: 15
<212> TYPE: PRT
<213> ORGANISM: Artificial Sequence
<220> FEATURE:
<223> OTHER INFORMATION: Synthetic construct of IgG1 hinge of B chain-
      IgG1 Fc(Y165T/T209F)

<400> SEQUENCE: 21

Glu Pro Lys Ser Cys Asp Lys Thr His Thr Cys Pro Pro Cys Pro
1               5                   10                  15

<210> SEQ ID NO 22
<211> LENGTH: 110
<212> TYPE: PRT
<213> ORGANISM: Artificial Sequence
<220> FEATURE:
<223> OTHER INFORMATION: Synthetic construct of IgG1 CH2 of B chain-IgG1
      Fc(Y165T/T209F)

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 23
<211> LENGTH: 107
<212> TYPE: PRT
<213> ORGANISM: Artificial Sequence
<220> FEATURE:
<223> OTHER INFORMATION: Synthetic construct of IgG1 CH3 of B chain-IgG1
      Fc(Y165T/T209F)

<400> SEQUENCE: 23

Gly Gln Pro Arg Glu Pro Gln Val Thr Thr Leu Pro Pro Ser Arg Asp
1               5                   10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35              40              45

Asn Asn Tyr Lys Thr Phe Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100             105

<210> SEQ ID NO 24
<211> LENGTH: 107
<212> TYPE: PRT
<213> ORGANISM: Homo sapiens

<400> SEQUENCE: 24

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
            35              40              45

Asn Asn Tyr Lys Thr Thr Pro Pro Val Leu Asp Ser Asp Gly Ser Phe
 50                      55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100             105
```

LONG-ACTING INSULIN OR INSULIN ANALOGUE CONJUGATE

CROSS REFERENCE TO RELATED APPLICATIONS

This application is a National Stage of International Application No. PCT/KR2016/001628 filed Feb. 17, 2016, claiming priority based on Korean Patent Application No. 10-2015-0024091 filed Feb. 17, 2015, the contents of all of which are incorporated herein by reference in their entirety.

TECHNICAL FIELD

The present invention relates to insulin and/or an insulin analogue conjugate with improved in vivo duration and stability due to the covalent linking between insulin and/or an analogue thereof and a biocompatible material capable of increasing in vivo half-life, and a use thereof. More specifically, the present invention relates to remarkable insulin and/or an insulin analogue conjugate, in which side effects caused by insulin treatment are reduced while administration compliance is improved because the property of in vivo durability is rendered therein, and a method for preparing the same. Additionally, the present invention provides a conjugate in which insulin and/or an insulin analogue and a biocompatible material capable of increasing in vivo half-life are linked by a covalent bond.

BACKGROUND ART

Insulin is a hormone secreted by the pancreas of the human body, which regulates blood glucose levels, and plays a role in maintaining normal blood glucose levels while carrying surplus glucose in the blood to cells to provide energy for cells. In diabetic patients, however, insulin does not function properly due to lack of insulin, resistance to insulin, and loss of beta-cell function, and thus glucose in the blood cannot be utilized as an energy source and the blood glucose level is elevated, leading to hyperglycemia. Eventually, urinary excretion occurs, contributing to development of various complications. Therefore, insulin therapy is essential for patients with abnormal insulin production (Type I) or insulin resistance (Type II), and blood glucose levels can be normally regulated by insulin administration.

Examples of the insulin formulations for treatment include not only native insulin but also insulin analogues under development, which have improved action time by modification of human insulin.

The first modified product of human insulin by genetic recombination technology was insulin lispro produced by Eli Lilly, where the order of the second lysine residue and the third proline residue on the carboxyl end of the B-chain were exchanged to block the formation of insulin dimers and hexamers, thereby increasing the amount of insulin monomers having excellent blood glucose level-lowering activity when administered via injection. Insulin aspart, produced by Novo Nordisk, is a modified insulin analogue, in which the proline residue at the $28^{th}$ position of the B-chain is substituted with an aspartic acid residue to increase the repulsion of the electric charge and block the formation of insulin hexamers, and is thereby capable of exhibiting a fast-acting activity of insulin. Insulin glulisine by Sanofi Aventis is a modified insulin analogue where the asparagine residue at the $3^{rd}$ position of the B-chain is substituted with a lysine residue and the lysine residue at the $29^{th}$ position of the B-chain is substituted with a glutamic acid residue to enable a rapid blood glucose level-lowering effect.

However, since insulin has an extremely short in vivo half-life, as is the case with other protein and peptide hormones, it is unable to show a long-acting therapeutic effect, and thus has a problem in that it must be administered continuously and repeatedly to exert its effect. Additionally, protein and peptide drugs are mostly administered to patients in the form of injections, and they are frequently injected to maintain concentration thereof in the blood, which causes severe pain to patients. Accordingly, studies have focused on the development of various protein formulations, chemical conjugates (e.g., fatty acid conjugates, polyethylene polymer conjugates), etc. to improve the therapeutic effects as well as the quality of patients' lives by reducing the frequency of administration through the increase of the in vivo half-life of these proteins.

In order to overcome these problems of insulin formulation administrations, as an example of various efforts, there has been an attempt to deliver an insulin drug into the body via inhalation through the oral or nasal cavity by increasing the biomembrane permeability of the insulin drug. An inhalable insulin agent for treating diabetes by Pfizer, "Exubera", was highlighted as a groundbreaking inhalable fast-acting insulin formulation for resolving the inconveniences of injection administration while exhibiting a blood glucose level-lowering effect similar to that of injection formulations of insulin; however, the formulation has been withdrawn from the market due to safety problems such as the risk of causing lung cancer and low sales performance. Additionally, many pharmaceutical firms including Novo Nordisk and Lilly have also stopped their research on the development of inhalable insulin.

The method of inhalation administration is certainly favored over the conventional injection administration method because the inhalation administration method is so simple that it can be performed by patients themselves without pain. However, the method has problems in that it has a lower efficiency of in vivo drug delivery than the injection formulations, and also has difficulties in maintaining the drug activity at a level required for its in vivo activity. Additionally, the method has difficulties in preparing compositions suitable for inhalation administration, such as contamination by microorganism and pathogenic bacteria, stability, durability, etc. Furthermore, the method of delivering an inhalable product into the lungs may have side effects of causing edema, cell damage, and inflammation in tissues. Accordingly, further studies are required on the mechanism of absorption by the lungs, but the current ability to predict absorption mechanism, absorption rate, and absorption range is still in its early stages.

However, many researchers and pharmaceutical firms still believe that it is possible to deliver insulin formulations through the respiratory tract, and thus they have continued to make efforts for the development thereof. At present, Afrezza, an inhalable insulin formulation by Mannkind Corporation that has overcome the drawbacks of Exubera, is undergoing FDA approval.

Additionally, administration methods capable of improving administration compliance and having a level of biological availability sufficient for effective treatment have been continuously developed for the past few years, as well as insulin formulations via administration routes for oral, nasal, and dermal absorption under clinical trials (E.-S. Khafagy et al., Advanced Drug Delivery Reviews; 59, (2007) 1521-1546).

Meanwhile, continuous efforts have been made to improve the stability of insulin formulation drugs in the blood and maintain long-acting high drug concentration in the blood, thereby maximizing drug efficacy and administration compliance. The long-acting formulations of insulin drugs should be able to improve the stability of insulin, and at the same time, maintain the titer of the drugs themselves at a high level, and should not induce a hypoglycemia reaction.

Examples of the long-acting insulin formulations currently available on the market may include insulin glargine (Lantus) of Sanofi-Aventis and insulin detemir (Levemir) of Novo Nordisk. The insulin glargine of Sanofi-Aventis is the first long-acting insulin, and was prepared by substituting the asparagine at the $21^{st}$ position of the A-chain with glycine while adding two arginine residues in the B-chain in order to provide solubility at an acidic pH condition and low solubility at an in vivo pH condition, thereby inducing the precipitation of insulin to be slowly absorbed when administered subcutaneously. The duration of insulin glargine is from about 20 hours to about 22 hours. The insulin glargine has advantages in that it acts longer than the fast-acting insulin (5 hours to 8 hours) and the superfast-acting insulin (3 hours to 5 hours) and does not cause hypoglycemia due to the absence of a peak of insulin concentration. The insulin detemir of Novo Nordisk is a long-acting insulin formulation developed most recently, and was prepared by deleting the threonine residue at the $30^{th}$ position of the B-chain while acylating the lysine residue at the $29^{th}$ position of the B-chain so that the insulin formulation can be conjugated to albumin when administered to humans, thereby providing a long-acting characteristic (Allison J. et al., DM. 148-162, 2010). The duration was developed to be in the range from 18 hours to 22 hours, slightly shorter than that of the insulin glargine, as a formulation to be administered once or twice daily. These long-acting insulin formulations have no peak for the insulin concentration in the blood and are thus suitable for base insulin. However, these long-acting insulin formulations do not have sufficient half-lives, and thus should be administered once or twice daily, thereby causing inconvenience to patients. In this regard, there is an urgent need for the development of a formulation capable of reducing administration frequency for diabetic patients who require long-term administration of diabetic drugs, thereby improving patient convenience.

DISCLOSURE

Technical Problem

The present inventors have made efforts to develop a long-acting insulin formulation for improving the administration compliance by increasing the durability thereof in the blood. As a result, they have succeeded in preparing an insulin or insulin analogue conjugate, which is formed by linking an A-chain conjugate and a B-chain conjugate, wherein each of the A- and B-chains is linked to immunoglobulin constant regions capable of increasing half-life of the insulin and analogue thereof. Such a conjugate is expected to dramatically increase half-life and to improve the yield because the process of removing C-peptide during purification is not required.

Technical Solution

An object of the present invention is to provide insulin and/or an insulin analogue conjugate capable of prolonging in vivo half-life and maintaining a hypoglycemic effect of insulin, in which an insulin analogue and a biocompatible material capable of prolonging half-life are conjugated thereto by a peptide bond.

Another object of the present invention is to provide insulin or an insulin analogue conjugate, in which insulin and/or an analogue thereof are conjugated to a biocompatible material capable of prolonging half-life by a peptide bond.

Still another object of the present invention is to provide a long-acting conjugate, which is insulin and/or an insulin analogue conjugate of the following Formula 1.

$$X\text{-La-F1:Y-La-F2} \qquad \text{[Formula 1]}$$

wherein, in the above Formula,

X is an insulin A-chain or an A-chain of an insulin analogue;

L is a linker;

a is 0 or a natural number, with the proviso that each L is independent from each other when a is 2 or greater;

: is a chemical bond;

Y is an insulin B-chain or a B-chain of an insulin analogue; and

F1 and F2 comprise an immunoglobulin constant region and have an FcRn-binding site.

Still another object of the present invention is to provide a polynucleotide encoding the insulin and/or insulin analogue conjugate; a vector containing the polynucleotide; and a transformant containing the vector.

Still another object of the present invention is to provide insulin and/or an insulin analogue conjugate, in which each of A- and B-chain conjugates of insulin and/or an analogue thereof is encoded followed by being conjugated by a double bond.

Still another object of the present invention is to provide insulin or an insulin analogue conjugate, in which formation of a double bond between A- and B-chain conjugates is promoted due to a variation of a biocompatible material to which each of the A- and B-chains of insulin and/or an analogue thereof is conjugated.

Still another object of the present invention is to provide a composition for preventing or treating diabetes, containing the insulin and/or insulin analogue conjugate.

Still another object of the present invention is to provide a method for treating diabetes, comprising administering the insulin and/or insulin analogue conjugate to a subject in need thereof.

Still another object of the present invention is to provide a method for preparing insulin and/or an insulin analogue conjugate, in which each of A- and B-chain conjugates of insulin and/or an analogue thereof is encoded followed by being conjugated by a double bond.

Still another object of the present invention is to provide a method for preparing insulin and/or an insulin analogue conjugate, in which each of A- and b-chain conjugates of insulin and/or an analogue thereof is encoded followed by being conjugated by a double bond, wherein the method is devoid of the removal of C-peptide after a refolding process.

Advantageous Effects of the Invention

The insulin and/or insulin analogue conjugate of the present invention can stably maintain the blood glucose level-lowering effect and increase half-life in blood, and is thus capable of improving administration compliance of insulin and reducing side effects of insulin treatment.

BEST MODE

In order to achieve the objects above, in an aspect, the present invention provides insulin and/or an insulin analogue conjugate capable of prolonging in vivo half-life and maintaining a hypoglycemic effect of insulin, wherein insulin and/or an analogue thereof and a biocompatible material capable of prolonging half-life are conjugated thereto by a peptide bond, or a method for preparing the same.

In an exemplary embodiment, the insulin and/or insulin analogue conjugate is a long-acting conjugate of the following Formula 1.

X-La-F1:Y-La-F2    [Formula 1]

wherein, in the above Formula,

X is a wild-type insulin A-chain or an analogue thereof;

L is a linker;

a is 0 or a natural number, with the proviso that each L is independent from each other when a is 2 or greater;

: is a chemical bond;

Y is a wild-type insulin B-chain or an analogue thereof; and

F1 and F2 comprise an immunoglobulin constant region and have an FcRn-binding site.

In another exemplary embodiment, the biocompatible material is an immunoglobulin Fc region.

In still another exemplary embodiment, the insulin or insulin analogue conjugate is insulin or an insulin analogue conjugate, in which each chain of the insulin analog is linked to each fragment of an immunoglobulin Fc region.

The linkage between each chain of insulin or an analogue thereof and each fragment of an immunoglobulin Fc region can be made at the gene level, and such linkage can be carried out by a high-molecular weight polymer such as polyethylene glycol (PEG).

In another aspect, the present invention provides insulin or an insulin analogue conjugate, in which insulin or an analogue thereof is conjugated to a biocompatible material capable of prolonging half-life by a peptide bond, or a method for preparing the same.

In still another aspect, the present invention provides a polynucleotide encoding the insulin and/or insulin analogue conjugate; a vector containing the polynucleotide; and a transformant containing the vector.

In still another aspect of the present invention, the insulin and/or insulin analogue conjugate are characterized by insulin and/or an insulin analogue conjugate, which are formed by linking A- and B-chain conjugates after each of the A- and B-chain conjugates is encoded.

In still another aspect of the present invention, the immunoglobulin Fc region, which is a biocompatible material forming the insulin and/or insulin analogue conjugate, is characterized by a biocompatible material in which a double bond is enhanced due to a variation.

In still another aspect, the present invention provides a composition for preventing or treating diabetes, containing the insulin and/or insulin analogue conjugate.

In an exemplary embodiment, the composition is characterized in that it includes one or more of the following features: (i) an improved effect of lowering blood glucose levels compared with insulin; (ii) an improved duration in the blood compared with insulin; (iii) maintenance of in vivo activity; and (iv) a reduced hypoglycemia effect as a side effect compared with insulin.

Hereinafter, the present invention will be described in more detail.

In an exemplary embodiment, the present invention provides insulin and/or an insulin analogue conjugate.

In an exemplary embodiment of the present invention, the insulin conjugate or insulin analogue conjugate is a single-chain linked material in which a moiety of insulin or an insulin analogue is conjugated to a moiety of an immunoglobulin Fc fragment via an amino acid linker or a non-amino acid linker by a peptide bond.

In another exemplary embodiment of the present invention, the insulin and/or insulin analogue conjugate may be those which form multimers, such as dimers, trimers, etc., through chemical association of two or more chains of linked materials. Herein, the chemical association is a concept including all chemical bonds, such as covalent bonds, ionic bonds, salt bridges, etc., and intermolecular forces, such as Van der Waals forces, hydrophobic interactions, etc., but is not limited thereto. In one exemplary embodiment of such multimers, the chemical association is a disulfide bond formed between Fc fragment moieties of different linked materials belonging to an identical conjugate. A further specific form of the insulin and/or insulin analogue conjugate of the present invention is formed by dimers associated with the above-described two linked materials of insulin or insulin analogue. Herein, moieties of insulin or insulin analogue in each of the insulin or insulin analogue linked materials forming the dimer, may be identical to each other. For example, a pair of the insulin and/or insulin analogue moieties o present in the dimeric form of the conjugate may be all wild-type B chains, i.e., the same homo-dimers. Alternatively, one moiety of insulin and/or an analogue may be insulin A-chain analogues while the other moiety of the insulin and/or analogue may be wild-type B-chain i.e., hetero-dimers. In an exemplary embodiment of the thus-described particular hetero-dimers, there may be no direct linkage between the moieties of the insulin A-chain (or an analogue thereof) and the insulin B-chain (of an analogue thereof) which makes a pair therewith, or alternatively these may be linked by a disulfide bond. Such disulfide bond may be the same or a different disulfide bond present between the formed wild-type insulin A- and B-chains.

In still another exemplary embodiment of the present invention, an insulin analogue may be used to resolve the problems of long-acting characteristic and hypoglycemia of insulin formulations.

As used herein, the term "insulin analogue" is an insulin variant of human possessing an in vivo blood glucose level-lowering characteristic similar to that of insulin, thereby referring to a peptide in which one or more amino acid sequences of wild-type or native insulin, A-chain, B-chain, and C-peptide are different.

The amino acid sequence of the native insulin is as follows.

A-chain:
(SEQ ID NO: 1)
Gly-Ile-Val-Glu-Gln-Cys-Cys-Thr-Ser-Ile-Cys-Ser-

Leu-Tyr-Gln-Leu-Glu-Asn-Tyr-Cys-Asn

B-chain:
(SEQ ID NO: 2)
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The insulin variant of the present invention refers to a peptide having an in vivo blood glucose-controlling capability, in which one or more insulins and amino acid sequences are different with insulin.

The insulin analogue of the present invention may include a peptide containing any one selected from the A-chain, the B-chain, and the C-peptide, and each of the amino acid sequences of the A-chain, the B-chain, and the C-peptide may be a wild-type sequence, or a sequence in which one or more wild-type or non-wild-type amino acids are added, substituted, or deleted in the native sequence, but is not limited thereto.

The insulin analogue of the present invention has a homology of at least 80% to each of the amino acid sequences of the A-chain, B-chain, and C-peptide of native insulin, and it may be in the form of a peptide, where a part of the groups in the amino acid residues is modified by chemical substitution (e.g., alpha-methylation, alpha-hydroxylation), deletion (e.g., deamination), or modification (e.g., N-methylation), and may include all peptides having an in vivo blood glucose level-controlling capability, but it is not limited thereto.

The insulin analogue of the present invention refers to a peptide having an in vivo blood glucose level-controlling capability equivalent to that of the insulin as describe above, and may include insulin agonists, derivatives, fragments, variants, etc., but it is not limited thereto.

The insulin agonist of the present invention refers to a material which can bind to an in vivo receptor of insulin regardless of the structure of insulin, and thereby, exhibit a biological activity equivalent to that of insulin.

The insulin fragment of the present invention refers to a form in which at least one amino acid is added or deleted, and the amino acid added may be one that is not present in nature (e.g., D-type amino acid), and such insulin fragment has an in vivo blood glucose level-controlling capability.

The methods of the present invention used in preparing the insulin agonists, derivatives, fragments, and variants may be used independently or in combination. For example, those having the in vivo blood glucose level-controlling capability, which have different in at least one amino acid sequence, and in which the amino acid residue in the amino terminus is deaminated, may be included.

In an exemplary embodiment, the present invention provides long-acting insulin and/or an insulin analogue conjugate, in which insulin and/or an analogue thereof is conjugated to a biocompatible material which is capable of prolonging half-life.

In another exemplary embodiment, the present invention provides a long-acting insulin conjugate in which insulin and/or an analogue thereof is conjugated to a biocompatible material selected from the group consisting of polyethylene glycol, fatty acid, cholesterol, albumin and a fragment thereof, an albumin-binding material, a polymer of repeating units of particular amino acid sequences, an antibody, an antibody fragment, an FcRn-binding material, an in vivo connective tissue or a derivative thereof, a nucleotide, fibronectin, transferrin, a saccharide, and a high-molecular weight polymer.

As used herein, the term "biocompatible material" refers to a material which, when covalently linked to insulin and/or an analogue thereof to form a conjugate, can increase in vivo half-lives of insulin and/or an analogue thereof, and thereby prolong the duration of the activities thereof. For example, since the main objectives are to increase half-lives and to maintain bioavailability and sustained duration of the materials, the biocompatible material which can be conjugated to insulin or an analogue thereof may include various biocompatible materials without limitation, for example, polyethylene glycol, fatty acid, cholesterol, albumin and a fragment thereof, an albumin-binding material, elastin, a water-soluble elastin precursor, a polymer of repeating units of a partial amino acid sequence of elastin, a polymer of repeating units of particular amino acid sequences, an antibody, an antibody fragment, an FcRn-binding material, an in vivo connective tissue, a nucleotide, fibronectin, transferrin, a saccharide, a high-molecular weight polymer, etc. Additionally, the insulin and/or analogue thereof may be conjugated to a biocompatible material capable of prolonging in vivo half-life by genetic recombination technology. The FcRn-binding material may be an immunoglobulin Fc region.

The insulin and/or analogue thereof of the present invention have lower activity compared to those of native insulin. Having a lower activity than those of native insulin suggests that they can lower the risk of hypoglycemia, which is the most serious problem of native insulin, and long-acting type formulations thereof have an advantage in that they can control blood glucose levels for a long period of time without the risk of hypoglycemia by continuously maintaining the low activity.

For example, the insulin conjugate and/or insulin analogue conjugate used in the present invention are characterized in that the biocompatible material or an immunoglobulin Fc fragment is conjugated to the carboxyl end by a peptide bond.

In an exemplary embodiment, the present inventors can produce insulin and/or an insulin analogue conjugate by fusing the A-chain or the B-chain of insulin and/or an analogue thereof at the amino end in the immunoglobulin Fc region at the gene level, followed by cloning the same into an expression vector.

The immunoglobulin Fc region is a biodegradable polypeptide that can be metabolized in vivo and is thus safe for use as a drug carrier. Additionally, the immunoglobulin Fc region has a lower molecular weight relative to the entire immunoglobulin molecule, and thus it has advantages in preparation, purification, and yield of a conjugate. Furthermore, due to the removal of Fab parts with high heterogeneity considering the variations in amino acid sequences among antibodies, the homogeneity of materials can be significantly increased and the possibility of inducing antigenicity in the blood can also be lowered.

The insulin and/or analogue thereof used in the present invention are linked to an immunoglobulin Fc region by a peptide bond and then produced in an expression host. The expression host may be a microorganism, such as *E. coli*, which can produce a protein by transforming a foreign gene, without limitation, and may be yeast, an insect cell, an animal cell, etc.

The Fc regions in the A- and B-chain conjugates of the insulin and/or insulin analogue produced by an expression host are conjugated to each other by a double bond during the folding process after the expression and then the A-chain and B-chain are linked, thus producing insulin and/or insulin analogue conjugate.

That is, insulin and/or an insulin analogue conjugate can be produced by promoting hetero-dimerization, instead of promoting homo-dimers of the A- and B-chain conjugates.

The double bond may be a disulfide bond.

The variations of the Fc regions of the present invention, such as substitution of tyrosine, which is the amino acid at the $9^{th}$ position of wild-type CH3 region of SEQ ID NO: 24, with threonine; substitution of serine, which is the amino acid at the $24^{th}$ position of wild-type CH3 region of SEQ ID NO: 24, with histidine; substitution of threonine, which is the amino acid at the 54$^{th}$ position of wild-type CH3 region of SEQ ID NO: 24, with phenylalanine; and substitution of phenylalanine, which is the amino acid at the position 65$^{th}$ position of wild-type CH3 region of SEQ ID NO: 24, with alanine, to promote a double bond, and as a result, insulin and/or an insulin analogue conjugate can be produced. However, the variations of amino acids, which not only include the substitutions of the amino acids above but also promote a double bond, can be included without limitation, and the variations are possible through various combinations. In the exemplary embodiments of the present invention, as a representative example, IgG1 was used as the Fc region for production, but IgG2, IgG3, IgG4, etc. are included without limitation.

As used herein, the term "immunoglobulin constant region" may be a constitution forming a moiety of insulin and/or an insulin analogue conjugate, and may comprise an immunoglobulin Fc region. In addition, the immunoglobulin constant region refers to the heavy chain constant region 2 (CH2) and the heavy chain constant region 3 (CH3) of an immunoglobulin, excluding variable regions of the heavy and light chains, the heavy chain constant region 1 (CH1), and the light chain constant region 1 (CL1) thereof, and may include a hinge region in the heavy chain constant region.

The immunoglobulin constant region of the present invention may include 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination of one or two or more domains and an immunoglobulin hinge region (or a part of the hinge region); or 6) a dimer of each domain of the heavy chain constant region and the light chain constant region.

Additionally, the immunoglobulin Fc region of the present invention not only includes its native amino acid sequence but also a sequence derivative thereof (a mutant). As used herein, an amino acid sequence derivative refers to an amino acid sequence which is different from the native amino acid sequence due to a deletion, an insertion, a non-conservative substitution, a conservative substitution, or a combination thereof in at least one amino acid residue. For example, in an IgG Fc, the amino acid residues at positions 214 to 238, 297 to 299, 318 to 322, or 327 to 331, which are known to be important in binding, may be used as appropriate sites for modification. Additionally, various kinds of other derivatives may be prepared by removing the sites for forming a disulfide bond, removing a few amino acids at the N-terminus of a native Fc, inserting a methionine residue at the N-terminus of a native Fc, etc. Additionally, to remove effector functions, a complement-binding site, e.g., a C1q-binding site, may be removed or an antibody dependent cell mediated cytotoxicity (ADCC) site may be removed. The techniques for preparing these sequence derivatives of the immunoglobulin Fc region are disclosed in International Publication Nos. WO 97/34631 and WO 96/32478.

Amino acid exchanges in proteins and peptides which do not alter the entire activity of molecules are known in the art (H. Neurath, R. L. Hill, The Proteins, Academic Press, New York, 1979). The most commonly occurring exchanges are exchanges between amino acid residues of Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Meanwhile, the immunoglobulin Fc region may be derived from humans or animals including cows, goats, pigs, mice, rabbits, hamsters, rats, and guinea pigs, and preferably from humans. Additionally, the immunoglobulin Fc region may be an Fc region that is derived from IgG, IgA, IgD, IgE, and IgM, or combination thereof or an Fc region prepared by a hybrid thereof. Preferably, it is derived from IgG or IgM, which are among the most abundant proteins in human blood, and most preferably derived from IgG, which is known to enhance the half-lives of ligand-binding proteins.

On the other hand, as used herein, the term "combination" means that polypeptides encoding a single-chain immunoglobulin Fc region of the same origin are linked to a single-chain polypeptide of different origin to form a dimer or multimer. That is, a dimer or multimer may be formed from two or more fragments selected from the group consisting of IgG Fc, IgA Fc, IgM Fc, IgD Fc, and IgE Fc fragments.

As used herein, the term "hybrid" means that sequences corresponding to two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3, and CH4 of IgG Fc, IgM Fc, IgA Fc, IgE Fc, and IgD Fc, and may include a hinge region.

Meanwhile, IgG may be divided into IgG1, IgG2, IgG3, and IgG4 subclasses, and the present invention may include combinations and hybrids thereof, preferably, IgG2 and IgG4 subclasses, and most preferably, the Fc region of IgG4 rarely having effector functions such as complement dependent cytotoxicity (CDC), but it is not limited thereto.

Specifically, the immunoglobulin Fc region, which is a moiety of the insulin and/or insulin analogue conjugate of the present invention, may be a human IgG1-derived Fc region, but Fc regions that can be used as a moiety of a conjugate are included without limitation. The human-derived Fc region is more preferable to a non-human derived Fc region which may act as an antigen in the human body and cause undesirable immune responses such as the production of a novel antibody against the antigen.

Such insulin or insulin analogue conjugate of the present invention can not only maintain the existing in vivo activity of insulin, such as energy metabolism and sugar metabolism, but can also markedly increase the serum half-life of insulin analogues, and subsequently, significantly increase the in vivo duration of the peptide, and is thus useful for the treatment of diabetes.

In an exemplary embodiment, the present invention provides a conjugate of the following Formula 1.

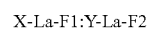  [Formula 1]

wherein, in the above Formula,

X is an insulin A-chain or an A-chain of an insulin analogue;

L is a linker;

a is 0 or a natural number, with the proviso that each L is independent from each other when a is 2 or greater;

: is a chemical bond;

Y is an insulin B-chain or a B-chain of an insulin analogue; and

F1 and F2 include an immunoglobulin constant region and have an FcRn-binding site.

Specifically, the chemical bond (:) of the conjugate may be a double bond between F1 and F2, i.e., the Fc regions, during the folding process after the expression of [X-La-F1] and [Y-La-F2], and as a result, the A-chain conjugate and B-chain conjugate may be in the form of a hetero-dimer. The chemical bond may be a disulfide bond, but is not limited thereto.

The F1 and F2 may be non-wild-type immunoglobulin regions with amino acid substitution(s), and the F2 and F1 may be immunoglobulin regions in which amino acids are substituted in different combinations, but these are not limited thereto.

In another exemplary embodiment, the B-chain of the insulin analogue may have one or more amino acids selected from the group consisting of amino acids at the $1^{st}$, $2^{nd}$, $3^{rd}$, $5^{th}$, $10^{th}$, $12^{th}$, $16^{th}$, $23^{rd}$, $24^{th}$, $25^{th}$, $26^{th}$, $27^{th}$, $28^{th}$, $29^{th}$, and $30^{th}$ positions of the insulin B-chain, which are deleted or substituted with other amino acids. For example, the B-chain of the insulin analogue may have one or more amino acids selected from the group consisting of amino acids at the $1^{st}$, $2^{nd}$, $3^{rd}$, $5^{th}$, $6^{th}$, $10^{th}$, $12^{th}$, $16^{th}$, $23^{rd}$, $24^{th}$, $25^{th}$, $26^{th}$, $27^{th}$, $28^{th}$, $29^{th}$, and $30^{th}$ positions of the insulin B-chain, which are substituted with other amino acids.

In still another exemplary embodiment, the A-chain of the insulin analogue may have one or more amino acids selected from the group consisting of amino acids at the $1^{st}$, $10^{th}$, $12^{th}$, $14^{th}$, $16^{th}$, $17^{th}$, $18^{th}$, $19^{th}$, and $21^{st}$ positions of the insulin A-chain, which are deleted or substituted with other amino acids. For example, the A-chain of the insulin analogue may have one or more amino acids selected from the group consisting of amino acids at the $1^{st}$, $2^{nd}$ $5^{th}$, $8^{th}$, $10^{th}$, $12^{th}$, $14^{th}$, $16^{th}$, $17^{th}$, $18^{th}$, $19^{th}$, and $21^{st}$ positions of the insulin A-chain, which are substituted with other amino acids.

In still another exemplary embodiment, the insulin analogue has one or more amino acids selected from the group consisting of amino acids at the $8^{th}$, $23^{rd}$, $24^{th}$, and $25^{th}$ positions of the B-chain and amino acids at the $1^{st}$, $2^{nd}$, $14^{th}$, and $19^{th}$ positions of the A-chain, which are substituted with other amino acids.

In still another exemplary embodiment, the substituted amino acids may be selected from the group consisting of alanine, glutamic acid, asparagine, isoleucine, valine, glutamine, glycine, lysine, histidine, cysteine, phenylalanine, tryptophan, proline, serine, threonine, and aspartic acid.

In still another exemplary embodiment, the substituted amino acids may be one or more amino acids selected from the group consisting of amino acids at the $8^{th}$, $23^{rd}$, $24^{th}$, and $25^{th}$ positions of the B-chain and amino acids at the $1^{st}$, $2^{nd}$ and $19^{th}$ positions of the A-chain, which are substituted with alanine, or alternatively the substituted amino acids may be the $14^{th}$ amino acid of the A-chain, substituted with glutamic acid or asparagine, but these are not limited thereto.

In still another exemplary embodiment, L is selected from the group consisting of peptides, polyethylene glycols, fatty acids, saccharides, high-molecular weight polymers, low-molecular weight compounds, nucleotides, and combinations thereof.

In still another exemplary embodiment, X and F1, and Y and F2 are linked to each other by L in a covalent chemical bond, a non-covalent bond, or a combination thereof.

In still another exemplary embodiment, F is an IgG Fc region.

Another aspect of the present invention is a polynucleotide encoding the insulin or analogue thereof; an expression vector containing the polynucleotide; and a transformant containing the expression vector.

The insulin and/or analogue thereof are the same as explained previously.

The polynucleotide refers to a deoxyribonucleotide (DNA) or a ribonucleotide (RNA), existing in a single- or double-stranded form, including genomic DNA, cDNA, and RNA being transcribed therefrom, and a nucleotide as the basic constituting unit not only includes natural nucleotides but also includes analogues having modifications in a sugar or base (Scheit, Nucleotide Analogs, John Wiley, New York, 1980; Uhlman and Peyman, Chemical Reviews, 90: 543-584, 1990). The polynucleotide of the present invention may be isolated or prepared using standard technology in molecular biology.

The recombinant vector according to the present invention may be constructed as a vector for typical cloning or expression, and may be constructed as a vector to use a prokaryotic cell or a eukaryotic cell as a host cell.

As used herein, the term "vector" refers to a recombinant vector capable of expressing a target protein in an appropriate host cell, which is a nucleic acid construct including essential regulatory factors operably linked to enable the expression of a nucleic acid insert. The present invention can prepare a recombinant vector which includes a nucleic acid encoding insulin or an analogue thereof. In addition, the insulin and/or analogue thereof may be obtained via transformation or transfection of the recombinant vector into a host cell.

In the present invention, the nucleic acid encoding insulin and/or an analogue thereof is operably linked to a promoter. As used herein, the term "operably linked" refers to a functional connection between a regulatory sequence for nucleic acid expression (e.g., a promoter, a signal sequence, a ribosome-binding site, a transcription termination sequence, etc.) and a different nucleotide sequence, and the regulatory sequence can regulate the transcription and/or translation of the different nucleotide sequence by the same.

As used herein, the term "promoter" refers to an untranslated nucleic acid sequence located upstream of a coding region, which includes a polymerase-binding site and has the activity of initiating transcription of a gene located downstream of a promoter into mRNA, i.e., a DNA domain to which polymerase binds and initiates the transcription of a gene, and it is located at the 5' domain of mRNA transcription initiation.

For example, when the vector of the present invention is a recombinant vector and uses a prokaryotic cell as a host cell, in general, a strong promoter (e.g., tac promoter, lac promoter, lacUV5 promoter, lpp promoter, pLλ promoter, pRλ promoter, rac5 promoter, amp promoter, recA promoter, SP6 promoter, trp promoter, T7 promoter, etc.) capable of executing transcription, a ribosome-binding site for the initiation of translation, and transcription/translation termination sequences should be included.

Additionally, the vector to be used in the present invention may be prepared by manipulating the plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4, λ-Charon, λCharon, λΔz1 and M13, etc.) or viruses (e.g., SV40, etc.) which are commonly used in the art, but is not limited thereto.

Meanwhile, when the vector of the present invention is a recombinant vector and uses a eukaryotic cell as a host cell, promoters derived from the genomes of mammalian cells (e.g., metallothionein promoter) or promoters derived from the mammalian viruses (e.g., adenovirus late promoter, 7.5K promoter of papillomavirus, SV40 promoter, cytomegalovirus promoter, and tk promoter of HSV) may be used, and in general, includes a polyadenylated sequence (e.g., bovine growth hormone terminator and a polyadenylated sequence derived from SV40) as a transcription termination sequence.

Additionally, the recombinant vector of the present invention includes an antibiotic-resistance gene commonly used in the art as a selective marker, and may include, for example, genes having resistance to ampicillin, gentamycin, carbenicillin, chloramphenicol, streptomycin, kanamycin, geneticin, neomycin, and tetracycline.

The recombinant vector of the present invention may additionally include a sequence so as to facilitate the purification of the target protein being collected, i.e., insulin and/or an analogue thereof. The sequence to be additionally included may be a tag sequence for protein purification, e.g., glutathione S-transferase (Pharmacia, USA), a maltose-binding protein (NEB, USA), FLAG (IBI, USA), hexahistidine, etc., but the kinds of the sequence necessary for the purification of target proteins are not limited thereto.

Fusion proteins expressed by the recombinant vector including the above tag sequence may be purified by affinity chromatography. For example, when glutathione S-transferase is fused, glutathione, which is the substrate of the enzyme, may be used, and when 6 histidine tags are used, a target protein may be easily collected by a Ni-NTA column.

A transformant in which the above vector is transformed may be constructed using a recombinant vector including a polynucleotide encoding the insulin and/or analogue thereof.

As used herein, the term "transformation" refers to a process of introducing DNA into a host cell and making the DNA to be replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, a Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation, a transformation using PEG, dextran sulfate-, lipofectamine-, and dry/suppression-mediated transformations, etc.

The method for transforming the recombinant vector including a nucleic acid encoding the insulin and/or analogue thereof according to the present invention may not be limited to these methods, but any method for transformation of transfection commonly used in the art may be used without limitation.

The transformant of the present invention may be obtained by introducing a recombinant vector including the target nucleic acid which encodes insulin and/or an analogue thereof into a host cell.

An appropriate host to be used in the present invention may not be particularly limited, but any hosts that can express the nucleic acid of the present invention may be used. Examples of the appropriate host may include bacteria belonging to the genus *Escherichia* such as *E. coli*, bacteria belonging to the genus *Bacillus* such as *Bacillus subtilis*, bacteria belonging to the genus *Pseudomonas* such as *Pseudomonas putida*, yeasts such as *Pichia pastoris, Saccharomyces cerevisiae*, and *Schizosaccharomyces pombe*, insect cells such as *Spodopterafrugiperda* (SF9), and animal cells such as CHO, COS, and BSC, but are not limited thereto.

In still another exemplary embodiment, the present invention provides a pharmaceutical composition for treating diabetes, containing the insulin and/or insulin analogue conjugate of the present invention.

The composition above has one of the following characteristics: (i) an improved effect of lowering blood glucose levels compared with insulin; (ii) an improved duration in the blood compared with insulin; (iii) maintenance of in vivo activity; and (iv) a reduced hypoglycemic effect as a side effect compared with insulin.

MODE OF THE INVENTION

Hereinafter, the present invention will be described in more detail with reference to the following Examples. However, these Examples are for illustrative purposes only, and the invention is not intended to be limited by these Examples.

Example 1: Synthesis of Genes of A- and B-Chain Linked Materials of Native Insulin Immunoglobulin Fc regions were fused to each of the A-chain and the B-chain of native insulin at the gene level, and inserted into an expression vector, respectively.

Specifically, linked materials in which each of the following A-chain and B-chain of native insulin are included were synthesized (Table 1). Specifically, the immunoglobulin Fc region conjugated to the A-chain was synthesized using an immunoglobulin Fc region in which serine, the $24^{th}$ amino acid of the wild-type IgG1 CH3 region of SEQ ID NO: 24, was substituted with histidine and in which phenylalanine, the $65^{th}$ amino acid of the wild-type IgG1 CH3 region of SEQ ID NO: 24, was substituted with alanine. In addition, the immunoglobulin Fc region conjugated to the B-chain was synthesized using an immunoglobulin region in which tyrosine, the $9^{th}$ amino acid of the wild-type IgG1 CH3 region of SEQ ID NO: 24, was substituted with threonine and in which threonine, the $54^{th}$ amino acid of the wild-type IgG1 CH3 region of SEQ ID NO: 24, was substituted with phenylalanine.

TABLE 1

| | | | Sequence | SEQ ID NO: |
|---|---|---|---|---|
| A-chain-IgG1 Fc (S171H/F212A) | DNA (SEQ ID NO: 3) | A-chain | atgggcattgtggaacagtgctgtaccagcatttgta gtctatatcaacttgaaaattattgtaat | 8 |
| | | IgG1 hinge | gagcccaaatcatgcgataaaacccacacctgtccc ccatgcccg | 9 |
| | | IgG1 CH2 | gctccggaactcttaggtggccctagcgtatttctgtt cccgccgaagccgaaggatacgctgatgatctcac | 10 |

TABLE 1-continued

| | | Sequence | SEQ ID NO: |
|---|---|---|---|
| | | ggaccccagaagttacttgcgtggtggtggacgtat cacatgaagatcccgaggtcaaatttaattggtacgt tgatggggttgaagtacataatgcaaaaacaaagcc gcgtgaggagcagtataattcaacttatcgtgtggtc agcgtgctgacagttctgcaccaggattggctcaac gggaaagaatataagtgtaaagtttccaacaaagcc ctgccagctcctatagagaaaactatctcgaaagcc aaa | |
| | IgG1 CH3 | ggacagccacgtgaacctcaggtttacacgctgcc accgtcccgcgatgaattaacaaaaaatcaggtgca tttgacgtgtctggttaagggtttctatccgagcgaca ttgcggtagaatgggaatctaatggacaacctgaga ataactacaaaactacaccgccggttttagatagcga tggttcctttgcgctttatagcaaactgacggtggaca aaagtcgttggcagcaaggcaacgtctttagttgca gcgtcatgcatgaagcacttcacaaccattacaccc agaaatctctgagcctgtcgcctggtaagtag | 11 |
| | Protein (SEQ ID NO: 4) A-chain | MGIVEQCCTSICSLYQLENYCN | 12 |
| | IgG1 hinge | EPKSCDKTHTCPPCP | 13 |
| | IgG1 CH2 | APELLGGPSVFLFPPKPKDTLMIS RTPEVTCVVVDVSHEDPEVKFN WYVDGVEVHNAKTKPREEQYNS TYRVVSVLTVLHQDWLNGKEYK CKVSNKALPAPIEKTISKAK | 14 |
| | IgG1 CH3 | GQPREPQVYTLPPSRDELTKNQV HLTCLVKGFYPSDIAVEWESNGQ PENNYKTTPPVLDSDGSFALYSK LTVDKSRWQQGNVFSCSVMHEA LHNHYTQKSLSLSPGK | 15 |
| B-chain-IgG1 Fc (Y165T/T209 F) DNA (SEQ ID NO: 5) | B-chain | atgtttgtaaatcaacatctgtgtgggagtcaccttgt ggaagcattatatttagtctgcggtgaacgtggattct tctacactcctaaaact | 16 |
| | IgG1 hinge | gaaccgaagtcatgcgataagacccatacgtgtcc gccctgtccc | 17 |
| | IgG1 CH2 | gccccggaactgcttggcggccctagtgttttttctgtt tcctccgaaaccaaaagatacgttgatgattagcag aacgccggaagttacctgtgtagtcgttgacgtatcc cacgaagatccggaggtgaaattcaattggtatgttg atggtgtggaggtgcataatgccaaaacgaaacctc gtgaagagcagtataactctacctaccgcgtcgtaa gcgtgctgacagttctccatcaggactggctgaatg gtaaagagtataaatgcaaagttagtaacaaggctct gcctgctcccatagaaaaaaccatctctaaagcgaa g | 18 |
| | IgG1 CH3 | ggtcagccgcgggagccacaagttacaaccctgcc accgtctcgcgacgaattaaccaagaatcaggtgtc cctgacatgcctagtcaagggcttttatcccagtgat attgcggtggaatgggaatcgaatggacaaccaga aaacaactacaaaactttcccgccagtcctggactc agatggcagcttttttctgtattctaaactcacagtgga taaatcgcgttggcagcaggggaacgtgtttagctg tagcgtgatgcatgaggcactgcacaatcattatact cagaaatcccttcattaagccctggaaaatag | 19 |
| | Protein (SEQ ID NO: 6) B-chain | MFVNQHLCGSHLVEALYLVCGE RGFFYTPKT | 20 |
| | IgG1 hinge | EPKSCDKTHTCPPCP | 21 |
| | IgG1 CH2 | APELLGGPSVFLFPPKPKDTLMIS RTPEVTCVVVDVSHEDPEVKFN | 22 |

TABLE 1-continued

| | Sequence | SEQ ID NO: |
|---|---|---|
| | WYVDGVEVHNAKTKPREEQYNS TYRVVSVLTVLHQDWLNGKEYK CKVSNKALPAPIEKTISKAK | |
| IgG1 CH3 | GQPREPQVTTLPPSRDELTKNQVS LTCLVKGFYPSDIAVEWESNGQP ENNYKTFPPVLDSDGSFFLYSKLT VDKSRWQQGNVFSCSVMHEALH NHYTQKSLSLSPGK | 23 |

Example 2: Preparation of Native Insulin Linked Material Exhibiting Polycistronic Expression After the synthesis of Example 1, the DNA fragment of the B-chain-IgG1 Fc linked material was inserted into a vector having the A-chain-IgG1 Fc linked material using a restriction enzyme in order to express the A-chain-IgG1 Fc linked material and B-chain-IgG1 Fc linked material, which were inserted into each of the expression vectors, in one vector. In order to construct a polycistronic expression system, an expression vector was constructed such that the genes of the above two linked materials were inserted into pET22b vector, an expression vector. Instead of cleaving the A-chain-IgG1 Fc linked material in the vector in which A-chain-IgG1 Fc was inserted, SalI and XhoI restriction sites, which are present in multi-cloning sites, were cleaved, and then the DNA fragment of the B-chain-IgG1 Fc linked material was inserted. For polycistronic expression, a ribosome-binding site was inserted in front of the B-chain-IgG1 Fc in order to form mRNA containing two ribosome-binding sites in a promoter. Thereafter, each of the A-chain-IgG1 Fc linked material and B-chain-IgG Fc linked material was expressed by these two ribosome-binding sites.

TABLE 2

| | Sequence | SEQ ID NO: |
|---|---|---|
| Sequence including ribosome-binding site | aataattttgtttaactttaagaaggaga TatacaA | 7 |

When the above polycistronic expression vector is expressed in a host cell, one long mRNA is formed within a vector. In addition, two proteins, which are the A-chain-IgG1 Fc linked material and the B-chain-IgG1 Fc linked material were expressed, respectively, via two ribosome-binding sites. The linked materials expressed were conjugated to each other by a double bond, and the transformed sites of the IgG1 CH3 were interlinked, and thus the A-chain-IgG1 Fc linked material and the B-chain-IgG1 Fc linked material could prepare an insulin conjugate capable of forming hetero-dimers. Such insulin conjugate may improve the yield because it does not require the step of removing C-peptide of an existing insulin conjugate, etc. after the refolding process when the insulin conjugate is expressed.

Accordingly, the insulin and/or insulin analogue conjugate can stably maintain the blood glucose level-lowering effect and increase the duration in blood, which remarkably increases serum half-life, and as a result, the insulin and/or insulin analogue conjugate of the present invention can be used as active ingredients of an insulin formulation capable of improving administration compliance thereof and reducing side effects.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

The invention claimed is:

1. A long-acting conjugate of the following Formula 1:

X-La-F1:Y-La-F2,   Formula 1 wherein, in the above Formula,
   X is a wild-type insulin A-chain or analogue thereof;
   L is a linker;
   a is 0 or a natural number, with the proviso that each L is independent from each other when a is 2 or greater;
   : is a chemical bond between F1 and F2;
   Y is a wild-type insulin B-chain or analogue thereof; and
   F1 and F2 each comprise a single chain polypeptide of immunoglobulin constant region and have an FcRn-binding site,
   wherein the chemical bond between F1 and F2 is a disulfide bond, and the long-acting conjugate forms a heterodimer via the disulfide bond, and
   wherein F1 is conjugated to carboxyl end of X via the linker L, and F2 is conjugated to carboxyl end of Y via the linker L.

2. The conjugate of claim 1, wherein each of the immunoglobulin constant region of F1 and F2 consists of 1 to 4 domains selected from the group consisting of CH1, CH2, CH3, and CH4 domains.

3. The conjugate of claim 2, wherein the immunoglobulin constant region is IgG.

4. The conjugate of claim 1, wherein each of the immunoglobulin constant region of F1 and F2 consists of a hinge region and 1 to 4 domains selected from the group consisting of CH1, CH2, CH3, and CH4 domains.

5. The conjugate of claim 1, wherein:
   F1 comprises a hinge region, CH2 region, and CH3 region of IgG1, in which serine, which is the amino acid at the 24th position of the wild-type CH3 region of SEQ ID NO: 24, is substituted with histidine, and phenylalanine, which is the amino acid at the 65th position of the wild-type CH3 region of SEQ ID NO: 24, is substituted with alanine; and
   F2 comprises a hinge region, CH2 region, and CH3 region of IgG1, in which tyrosine, which is the amino acid at the 9th position of the wild-type CH3 region of SEQ ID NO: 24, is substituted with threonine, and threonine, which is the amino acid at the 54th position of the wild-type CH3 region of SEQ ID NO: 24, is substituted with phenylalanine.

6. The conjugate of claim 1, wherein F1 and F2 are non-wild-type immunoglobulin regions with amino acid substitution(s), and wherein amino acid substitution(s) in the F2 and amino acid substitution(s) in the F1 are different from each other.

7. The conjugate of claim 1, wherein the linker L comprises a peptide or polyethylene glycol.

8. The conjugate of claim 1, wherein the insulin B-chain analogue has one or more amino acid substitutions at position(s) selected from the group consisting of amino acids at the 8th, 10th, 12th, 16th, 23rd, 24th, 25th, 26th, 27th, 28th, 29th, and 30th positions of the wild-type insulin B-chain,
wherein the wild-type insulin B-chain consists of the amino acid sequence of SEQ ID NO:2.

9. The conjugate of claim 1, wherein the insulin A-chain analogue has one or more amino acid substitutions at position(s) selected from the group consisting of amino acids at 1st, 2nd, 5th, 14th, 19th, and 21st positions of the wild-type insulin A-chain,
wherein the wild-type insulin A-chain consists of the amino acid sequence of SEQ ID NO:1.

10. A pharmaceutical composition comprising the conjugate of claim 1 and a pharmaceutically acceptable carrier.

11. A method for treating diabetes, comprising administering an effective amount of the conjugate of claim 1 to a subject in need thereof.

12. A method of preparing the conjugate of claim 1, comprising
   (a) preparing A-chain linked material in the form of [X-La-F1] and B-chain linked material in the form of [Y-La-F1];
   (b) preparing a vector comprising the linked materials; and
   (c) expressing the vector in a host cell to produce the conjugate,
wherein,
X is a wild-type insulin A-chain or analogue thereof;
L is a linker;
a is 0 or a natural number, with the proviso that each L is independent from each other when a is 2 or greater;
Y is a wild-type insulin B-chain or analogue thereof; and
F1 and F2 each comprise a single chain polypeptide of immunoglobulin constant region and have an FcRn-binding site,
wherein the chemical bond between F1 and F2 is a disulfide bond, and the long-acting conjugate forms a heterodimer via the disulfide bond, and
wherein F1 is conjugated to carboxyl end of X via the linker L, and F2 is conjugated to carboxyl end of Y via the linker L.

13. The method of claim 12, wherein the (c) step comprises a refolding process of the linked materials.

14. The method of claim 13, wherein the method is characterized in that the method is devoid of the removal of C-peptide after the refolding process.

15. The method of claim 12, wherein:
F1 comprises a hinge region, CH2 region, and CH3 region of IgG1, in which serine, which is the amino acid at the 24th position of the wild-type CH3 region of SEQ ID NO: 24, is substituted with histidine, and phenylalanine, which is the amino acid at the 65th position of the wild-type CH3 region, is substituted with alanine; and
F2 comprises a hinge region, CH2 region, and CH3 region of IgG1, in which tyrosine, which is the amino acid at the 9th position of the wild-type CH3 region of SEQ ID NO: 24, is substituted with threonine, and threonine, which is the amino acid at the 54th position of the wild-type CH3 region of SEQ ID NO: 24, is substituted with phenylalanine.

* * * * *